US006679922B1

(12) United States Patent
Sun et al.

(10) Patent No.: US 6,679,922 B1
(45) Date of Patent: *Jan. 20, 2004

(54) PESTICIDE PROTECTIVE ARTICLES

(75) Inventors: Gang Sun, Davis, CA (US); Louise L. Ko, Davis, CA (US); Takayuki Shibamoto, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 42 days.

This patent is subject to a terminal disclaimer.

(21) Appl. No.: 09/645,076

(22) Filed: Aug. 23, 2000

Related U.S. Application Data

(63) Continuation-in-part of application No. 09/102,525, filed on Jun. 22, 1998, now Pat. No. 6,077,319.

(60) Provisional application No. 60/151,667, filed on Aug. 31, 1999.

(51) Int. Cl.[7] .................... D06M 13/322; A01N 47/10; A61K 31/27

(52) U.S. Cl. ............................ 8/115.51; 8/189; 8/190; 514/478

(58) Field of Search ................................ 8/115.51, 190

(56) References Cited

U.S. PATENT DOCUMENTS

| | | | | |
|---|---|---|---|---|
| 2,934,451 A | | 4/1960 | Prichard et al. | 106/287 |
| 4,154,753 A | * | 5/1979 | Fielding | 558/29 |
| 4,201,822 A | | 5/1980 | Cowsar | 428/240 |
| 4,883,608 A | | 11/1989 | Trujillo et al. | 252/189 |
| 5,371,060 A | * | 12/1994 | Glock et al. | 504/106 |
| 5,490,983 A | * | 2/1996 | Worley et al. | 424/405 |
| 5,882,357 A | * | 3/1999 | Sun et al. | 8/189 |
| 6,017,955 A | * | 1/2000 | Gaglani et al. | 514/478 |
| 6,124,350 A | * | 9/2000 | Gaglani et al. | 514/478 |
| 6,228,885 B1 | * | 5/2001 | Palla et al. | 514/538 |

FOREIGN PATENT DOCUMENTS

WO WO9420118 A 9/1994

OTHER PUBLICATIONS

Database WPI, Section Ch, Week 199436, Derwent Publication Ltd., London, GB; AN 1994–291518, XP002157475 & KR 9 309 035B (Res Inst Nat Defence Sci), Sep. 22, 1993 abstract.

* cited by examiner

*Primary Examiner*—Yogendra N. Gupta
*Assistant Examiner*—Preeti Kumar
(74) *Attorney, Agent, or Firm*—Townsend and Townsend and Crew LLP

(57) ABSTRACT

The present invention provides methods for preparing an article capable of detoxifying a pesticide, such as textiles, comprising: (a) immersing the article in an aqueous treating solution which comprises a catalyst, a wetting agent and a heterocyclic amine; and (b) treating the article with a halogenated aqueous solution, thereby rendering the article capable of detoxifying a pesticide.

28 Claims, 7 Drawing Sheets

5,5-Dimethylhydantoin 2,2,5,5-Tetramethyl-4-imidazolidinone 4,5,5-Tetramethyl-2-imidazolidinone Triazine-1,3,5-trione Monomethoxymethyl-5,5-dimethylhydantoin 1,3-Dimethoxymethyl-5,5-dimethylhydantoin 5,5-Dimethylhydantoin 2,2,5,5-Tetramethyl-
4-imidazolidinone 4,5,5-Tetramethyl-
2-imidazolidinone Triazine-1,3,5-trione Monomethoxymethyl-
5,5-dimethylhydantoin 1,3-Dimethoxymethyl-
5,5-dimethylhydantoin

A

B

C

PESTICIDE PROTECTIVE ARTICLES

CROSS-REFERENCES TO RELATED APPLICATIONS

This Application U.S. patent application Ser. No. 09/102,525, filed Jun. 22, 1998, now U.S. Pat. No. 6,077,319 and U.S. Provisional Patent Application No. 60/151,667, filed Aug. 31, 1999, the teachings of which are incorporated herein by reference in their entirety for all purposes.

FIELD OF THE INVENTION

In general, this invention relates to methods for the protection against pesticides, and more particularly, this invention relates to processes for making articles capable of detoxifying pesticides.

BACKGROUND OF THE INVENTION

Due to the toxicity of pesticides, protection of agricultural and farm workers against exposure and contact is highly desirable. Without proper protection, dermal exposure to pesticides can lead to skin sensitization, cancer, birth defects and even death. One effective means of protection of agricultural field workers is by using protective clothing. Currently, pesticide protective clothing is made of disposable and non-permeable synthetic materials. These materials cannot be comfortably worn in all seasons due to the generation of heat stress to agricultural workers. In addition to the discomfort and impermeable properties of these materials, synthetic materials are non-biodegradable, thus, serious environmental concerns exist.

In general, the movement of pesticides on fabrics used for protective clothing can be characterized in terms of permeation and penetration (see, Easter, E. P. and Nigg, H. N., *Review of Environmental Contamination and Toxicology*, Vol. 129, 1992, p 1–15). Permeation is the process by which a chemical moves through a material on a molecular level. Such movement includes the sorption of molecules of the chemicals into the contacted surface of the material, the diffusion of the adsorbed molecules in the material and the desorption of molecules from the inside surface of the material into the collecting medium. Penetration, on the other hand, is the flow of a liquid chemical through closures, porous material, and material imperfections on a non-molecular level. In both cases, a physical barrier can effectively prevent any movement of pesticides through the fabrics. Materials that are considered as physical barriers to chemicals are those that will not allow any measurable movement of pesticides through them. Oftentimes, these barrier materials are specifically referred to as chemically resistant materials. Being thick and heavy, these chemical resistant materials disallow permeation and respiration at the same time, hence, generating tremendous heat stress and physical discomfort to wearers.

Since the surface contact of pesticides with materials such as fabrics, occurs by both permeation and penetration mechanisms, new methods are needed to decontaminate the pesticides on the fabrics. Methods are needed that will restrict the movement and infiltration of pesticides on the surface of the textiles such as workers' clothing. The present invention fulfills these as well as other needs.

SUMMARY OF THE INVENTION

Due to the high toxicity of pesticides and the concomitant high dermal absorption suffered by farm workers, protection of agricultural and farm workers against pesticide exposure and contact is imperative. As such, the present invention provides a process for making an article, such as a textile material, capable of detoxifying a pesticide, the process comprising:

(a) immersing the article in an aqueous treating solution which comprises a catalyst, a wetting agent and a heterocyclic amine; and (b) treating the article with a halogenated aqueous solution, thereby rendering the article capable of detoxifying a pesticide.

Surprisingly, the inventors have discovered that chemical detoxification of pesticides can be carried out on the surface of textile materials if a reactive chemical is permanently incorporated on the surface thereof. Consequently, the textile materials of the present invention provide outstanding protection as well as comfort.

The articles of the present invention include, but are not limited to, textiles such as cellulosic fabric, cellulosic yam, cellulosic fiber, cotton/polyester blends, cellulosic/synthetic blends, polymers such as synthetic polymers, wood products and the like. In a preferred aspect, the present invention provides shirt-weight cotton-containing apparel for field workers that are capable of detoxifying pesticides. The apparel that undergoes the processes of the present invention has the surprising advantage of being capable of detoxifying pesticides, thus rendering the apparel an excellent choice for farm workers. Moreover, the treated cotton fabrics are comfortable and breathable and thus, the workers' heat stress is also reduced.

In another aspect, the present invention provides a process for detoxifying a pesticide, comprising: contacting the pesticide with an article having an N-halamine attached thereto, thereby detoxifying the pesticide. As the pesticide comes in contact with fibrous materials of the articles upon permeation or penetration, chemical detoxification of the pesticides can be carried out on the surface of the treated textile materials or articles. In this aspect, a reactive chemical, such as a N-halamine, is permanently incorporated on the surface of the textile while maintaining integral textile properties. In certain aspects, the textile materials contain active functional groups such as chlorine, which have been discovered to be an excellent detoxifying agent in the decomposition of pesticides.

These and other aspects will become more readily apparent when read with the accompanied figures and the detailed description that follows.

DETAILED DESCRIPTION OF THE INVENTION AND PREFERRED EMBODIMENTS

Figure 1:
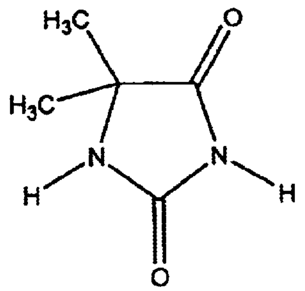
FIG. 1 illustrates suitable heterocyclic amines for use in present invention.
Figure 1:
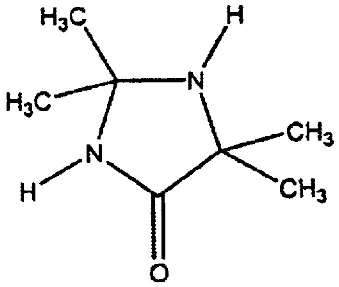
Figure 1:
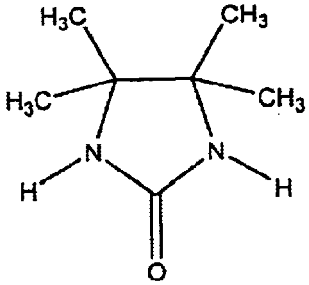
Figure 1:
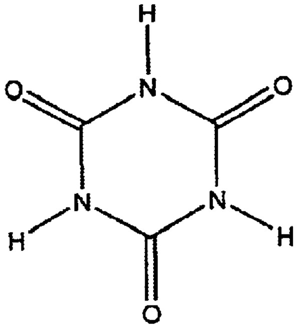
Figure 1:
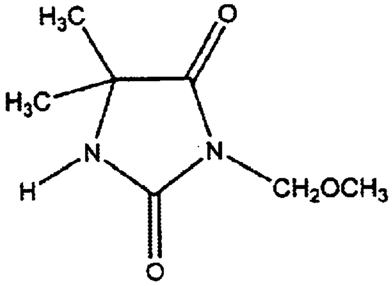
Figure 1:
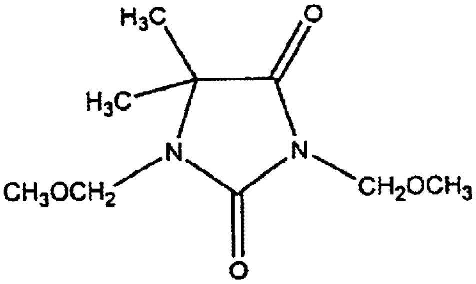

In certain embodiments, the present invention provides methods for making an article, such as a textile, capable of detoxifying a pesticide, comprising: (a) immersing the article in an aqueous treating solution which comprises a catalyst, a wetting agent and a heterocyclic amine; and (b) treating the article with a halogenated aqueous solution, thereby rendering the article capable of detoxifying a pesticide.

As used herein, the phrase "capable of detoxifying a pesticide" refers to the ability of the article to chemically convert the pesticide into a non-toxic fragment(s). Without being bound by any particular theory, it is believed that the article detoxifies the pesticide by a degradation mechanism, i.e., the articles that undergo the processes of the present invention are capable of chemically degrading the pesticides (e.g. by oxidation or oxidative hydrolysis). In preferred embodiments, the articles which undergo the processes of the present invention, have functional groups attached thereto rendering them capable of chemically reacting with the pesticides and thereby rendering the pesticide non-toxic. In certain instances, the pesticide is degraded into a:non-toxic derivative.

A wide variety of articles are suitable for use in the present invention. These articles include, but are not limited to, textiles such as cellulosic fabric, cellulosic yarn, and cellulosic fiber; polymers such as polyester and cellulose; cotton/polyester blends; cellulose/synthetic blends; wood materials such as wood pulp and paper; wood farming materials; tractor farming materials; garments such as shirts, pants, undergarments, coats, hoods, cloaks, gloves and protective garments. Those of skill in the art will know of other articles suitable for use in the processes of the present invention.

Using the methods of the present invention, the articles, such as textiles, offer protection against the toxic effects of pesticides, by for example, chemically oxidizing the pesticides. The article is immersed in an aqueous treating solution. The aqueous treating solution comprises a heterocyclic amine, optionally a wetting agent and optionally a catalyst. As used herein, "wetting agent" refers to a substance that increases the rate at which a liquid spreads across a surface, i.e., it renders a surface nonrepellent to a liquid. Examples of suitable wetting agents include, but are not limited to, TRITON® X-100 which is generically a polyoxyethylene (10) isooctylphenyl ether available from Sigma Chemical Co., St. Louis, Mo.; SEQUAWET® which is generically, a wetting agent containing nonionic surfactants available from Sequa Chemical Inc., Chester, S.C.; and AMWET® which is generically, a wetting agent containing nonionic surfactants available from American Emulsions Co., Dalton, Ga. Other wetting agents suitable for use in the present invention will be known to and used by those of skill in the art. As used herein, "catalyst" refers to a substance that augments the rate of a chemical reaction without itself being consumed. Suitable catalysts for use in the present invention include, but are not limited to, magnesium salts, zinc salts and ammonium salts. In a presently preferred embodiments, the catalysts include, but are not limited to, $MgCl_2$, $Mg(NO_3)_2$, $Zn(NO_3)_2$ and $NH_4NO_3$.

After the article, such as a fabric, is immersed in the above-described aqueous solution, the article is thereafter treated with a halogenated solution, such as a halogenated aqueous solution. The halogenated solution can be a chlorine solution, a bromine solution, a solution containing free chlorine or bromine, combinations thereof, etc. In a presently preferred embodiment, the halogenated solution is sodium hypochlorite (e.g., a chlorine bleach solution such as CLOROX®), or trichloro isocyanuric acid or sodium dichloro isocyanuric acid. The treatment of the article with a halogenated solution renders the article capable of detoxifying a pesticide.

In certain aspects of the present invention, several steps can optionally be inserted between step (a) and (b) above. For instance, in certain preferred aspects, the method further comprises removing excess aqueous treating solution from the article before treating the article with a halogenated aqueous solution. In this aspect, the excess aqueous treating solution is removed by ordinary mechanical methods, such as by passing the article (e.g., textile) between squeeze rolls, by centrifugation, by draining or by padding. In a preferred embodiment, the excess aqueous treating solution is removed by padding.

In addition, the process optionally further comprises drying the article after removing excess aqueous treating solution to produce a dried article. In this aspect, the article is dried at a temperature ranging from about 50° C. to about 90° C. and, more preferably, at a temperature ranging from about 75° C. to about 85° C. for a period of time ranging from about 3 to about 8 minutes and, more preferably, for about 5 minutes.

Moreover, the dried article can optionally be cured to produce a cured article. The curing process is conducted at a temperature ranging from about 120° C. to about 200° C. and, more preferably, at a temperature ranging from about 140° C. to about 160° C. for a period of time ranging from about 3 to about 8 minutes and, more preferably, for about 5 minutes. The heating can be carried out in an oven, preferably one having a forced draft of air directed at the surface of the article and exhausting through a vent to remove fumes.

The cured article is then optionally washed to remove excess reagents. Washing of the treated article can be done with water. The covalent bonds formed are stable, insoluble, and durable to the mechanical agitation, spraying and rubbing that occurs in washing machines or in large scale continuous or batchwise textile washing equipment. In certain preferred embodiments, the process further comprises drying the washed article to remove water.

The article can optionally be dried before treating the article with a halogenated aqueous solution, to render the article capable of detoxifying a pesticide. Drying of the article, such as a fabric, can be carried out by any ordinary means such as oven drying, line drying or, tumble drying in a mechanical clothes dryer. A drying temperature of about 60° C. to about 100° C. is particularly preferred. Suitable drying times are generally less than 15 minutes in duration.

certain preferred aspects, the present invention provides a process for preparing an article capable of detoxifying a pesticide, comprising: (a) immersing the article in an aqueous treating solution which comprises a catalyst, a wetting agent and a heterocyclic amine; (b) removing the excess treating solution from the article; (c) drying the article; (d) curing the article; (e) washing the cured article to remove excess reagents; (f) drying the washed article to remove water; and (g) treating the cellulosic article with a halogenated aqueous solution, thereby rendering an article capable of detoxifying a pesticide.

The articles become capable of detoxifying pesticides by grafting a heterocyclic N-halamine structure on the article.

Figure 2:
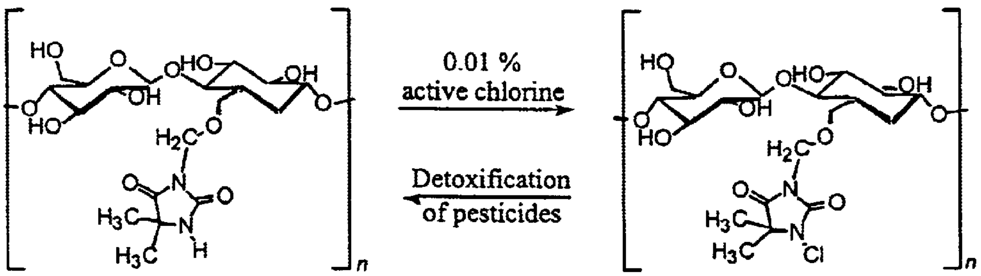
FIG. 2 illustrates formation of a N-halamine on cellulosic fabric and the subsequent detoxification.

With reference to FIG. 2, with incorporation of a halamine on a fabric such as cotton and subsequent halogenation, the article is thereby rendered capable of detoxifying a pesticide. "Heterocyclic amine," as used herein, refers to a 4- to 7-membered ring, having at least 3 members of the ring being carbon, and from 1 to 3 members of the ring being nitrogen, and from 0 to 1 member of the ring being an oxygen, wherein from 0 to 2 carbon members comprise a carbonyl group, and wherein at least 1 to 3 nitrogen atoms are substituted with a hydrogen or hydroxyalkyl group, such as $-CH_2OH$, or a alkoxyalkyl group, such as $-CH_2OCH_3$. Suitable heterocyclic amines are set forth in FIG. 1. Those of skill in the art will know of other heterocyclic amines suitable for use in the present invention. After halogenation, at least one ring nitrogen has bonded thereto a halogen atom. In addition, the ring members can be further substituted with alkyl groups, such as methyl, ethyl, etc., or hydroxy groups. Heterocyclic N-halamines are generally disclosed in U.S. Pat. No. 5,490,983 issued to Worley, et al. on Feb. 13, 1996, the teachings of which are incorporated herein by reference for all purposes.

The preferred heterocyclic amines suitable for use in the present invention include, but are not limited to, monomethylol-5,5-dimethylhydantoin (MDMH), 1,3-dimethylol-5,5-dimethylhydantoin (DMDMH); monoalkylolated and dialkylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid and 5,5-dimethylhydantoin; and monoalkoxylated and dialkoxylated derivatives of monoalkylolated and dialkylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid, 5,5-dimethylhydantoin, 2,2,5,5-tetramethyl-1,3-imidazolidin-4-one and mixtures thereof. Preferably the heterocyclic amine is monomethylol-5,5-dimethylhydantoin (MDMH), and 1,3-dimethylol-5,5-dimethylhydantoin (DMDMH) (see, FIG. 1).

Those of skill in the art will readily appreciate that the concentration of the various components of the aqueous treating solution can be widely varied depending upon the particular components employed and the results desired. Typically, the heterocyclic amine is present at a concentration of at least about 0.2%. More typically, the heterocyclic amine is present at a concentration ranging from about 0.2% to about 20%, more preferably at a concentration ranging from about 0.5% to about 10% and, more preferably at a concentration ranging from about 1% to about 5%. It will be readily apparent to those of skill in the art that higher heterocyclic amine concentrations (e.g., 50%) can be employed, but such higher concentrations are not required to impart pesticide-detoxifying activity. Again, suitable pesticide detoxifying activity can be imparted using a heterocyclic amine concentration as low as about 0.2%. The wetting agent is typically present at a concentration ranging from about 0.1% to about 3% and, more preferably, at a concentration ranging from about 0.2% to about 1%. The concentration of the catalyst employed will depend on the concentration of the heterocyclic amine employed. Typically, the ratio of heterocyclic amine to catalyst present will range from about 10:1 to about 5:1. The pH of the aqueous treating solution will typically range from a pH of about 2 to about 6 and, more preferably, from a pH of about 2.5 to about 4.5.

Those of skill in the art will readily appreciate that other additives can optionally be incorporated into the aqueous treating solution to impart favorable characteristics to the pesticide resistance articles. Such additives can include softeners and waterproofing agents that are known to and used by those of skill in the art. Examples of softeners which can be added to the aqueous treating solution include, but are not limited to, MYKON® and SEQUASOFT® both of which are commercially available from Sequa Chemical Inc. (Chester, S.C.). Examples of waterproofing agents which can be added to the aqueous treating solution include, but are not limited to, SEQUAPEL® (Sequa Chemical Inc., Chester, S.C.), SCOTCHGARD® (3M, St. Paul, Minn.) and other water repellent finishing solutions used by those of skill in the art.

Without being bound by any particular theory, it is believed in certain instances, that an active halogen, such as the N-halamine on a fabric, detoxifies the pesticide by chemical oxidation. The chemical oxidation occurs by contacting the pesticide with the N-halamine. For example, in the case of an N-halamine, the active halogen atom can effectively oxidize functional groups on pesticides, thereby detoxify the pesticide in the process. It is believed that the contact of pesticides with an article (e.g. textile materials) occurs by both permeation and penetration of the pesticides on the fabrics. Therefore, the fabric materials provide opportunities for chemical detoxification on the surface of the materials. As the pesticide is in contact with fibrous materials upon permeation or penetration, a large surface area of the fabric allows for the detoxification to occur. Thus, chemical detoxification of pesticides can be carried out on the surface of textile materials if a reactive chemical or functional group is permanently incorporated on the surface of the fabrics.

Figure 3:
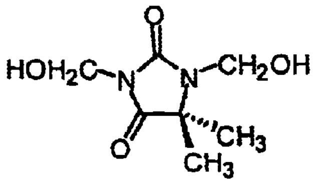
FIG. 3 Panel A illustrates the chemical formula of 1,3-dimethylol 5,5-dimethyl hydantoin (DMDMH); Panel B illustrates the chemical formula methomyl; and Panel C illustrates the chemical formula of aldicarb.
Figure 3:
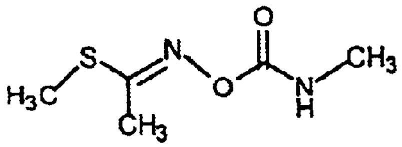
Figure 3:
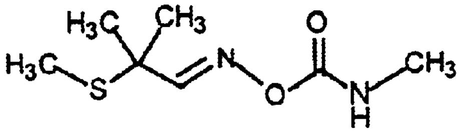

Using the methods of the present invention, it is possible to detoxify pesticides (e.g., methomyl and aldicarb; see, FIG. 3B–C) by contacting the pesticide with a grafted N-halamine structure on an article (e.g., cotton/polyester fabrics). For example, in the detoxification of methomyl, both the concentration of active chlorine present on the article and the concentration of methomyl being exposed to the article effect the detoxification efficiency. It is believed that the amount of active halogen on the fabric is directly proportional to the amount of pesticide reduced. Therefore, in certain aspects, for efficient detoxification of methomyl, it is preferable to graft DMDMH on the cotton/polyester fabric at a high add-on rate (e.g., 6%) with high active chlorine treatment (e.g., 0.1%).

As such, in another embodiment, the present invention provides a process for detoxifying a pesticide, comprising: contacting the pesticide with an article having an N-halamine attached thereto, thereby detoxifying the pesticide. A wide variety of pesticides can be detoxified using the methods of the present invention. These pesticides include, but are not limited to, herbicides, fungicides, rodenticides, insecticides and mixtures thereof. More particularly, suitable pesticides include, but are not limited to, methomyl, aldicarb, carbofuran, and carbaryl. Other pesticides which are detoxified using the processes of the present invention include, but are not limited to:

A. Benzo-2,1,3-thiodiazin-4-one-2,2-dioxides such as bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. 1,3-dimethylpyrazole derivatives such as pyrazoxyfen, pyrazolate and benzofenap;

D. Dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon, metoxuron, neburon, isoproturon, chlorotoluron, chloroxuron, linuron, monolinuron, chlorobromuron, daimuron and methabenzthiazuron;

G. phenylcarbamoyloxyphenylcarbamates such as phenmedipham and desmedipham;

H. 2-phenylpyridazin-3-ones such as chloridazon and norflurazon;

I. uracil herbicides such as lenacil, bromacil and terbacil;

J. triazine herbicides such as atrazine, simazine, aziprotryne, cyanazine, prometryn, dimethametryn, simetryne and terbutryn;

K. phosphorothioate herbicides such as piperophos, bensulide and butamifos;

L. thiolcarbamate herbicides such as cycloate, vemolate, molinate, thiobencarb, butylate, EPTC, triallate, diallate, ethyl esprocarb, tiocarbazil, pyridate and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, alachlor, propachlor, propanil, metazachlor, metolachlor, acetochlor and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or esters thereof, nitrofen, bifenox, acifluorfen and salts and esters thereof, oxyfluorfen and fomesafen; chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxydim, tralkoxydim and clethodim;

U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof, DPX-LS300 and pyrazosulfuron;

V. imidazolidinone herbicides such as imazaquin, imazamethabenz, imazapyr and isopropylammonium salts thereof, imazethapyr;

W. arylanilide herbicides such as flamprop and esters thereof, benzoylprop-ethyl, diflufenican;

X. amino acid herbicides such as glyphosate (ROUND-UP®) and glufosinate and their salts and esters, sulphosate and bilanafos;

Y. organoarsenical herbicides such as MSMA;

Z. herbicidal amide derivative such as napropamide, propyzamide, carbetamide, tebutam, bromobutide, isoxaben, naproanilide, diphenamid and naptalam;

AA. miscellaneous herbicides including ethofumesate, cinmethylin, difenzoquat and salts thereof such as the methyl sulfate salt, clomazone, oxadiazon, bromofenoxim, barban, tridiphane, flurochloridone, quinchlorac and mefanacet;

BB. examples of useful contact herbicides include bipyridylium herbicides such as those in which the active entity is paraquat and those in which the active entity is diquat.

CC. Pesticides developed for application over the top of genetically engineered crops (e.g., ROUND-UP® READY SOYBEANS).

It has been reported that the penetration of pesticides is influenced by a variety of factors. These factors include, geometrically oriented capillary forces, relative interfacial tensions between fabric surfaces and pesticide emulsions, polymeric composition of the fibers and total pesticide load on the fabrics. Amongst these factors, penetration and permeability are notably dependent on pesticide load on the fabrics (see, Obendorf, S. K. et al., *Archives of Environmental Contamination and Toxicology*, Vol. 21, 1991, p10–16). Consistent with these findings, a decrease in detoxification of certain pesticides (e.g., methomyl) was observed with an increase in pesticide concentration being loaded onto the fabric. Thus, in a preferred embodiment, the halamine is loaded using a high add-on rate.

In certain aspects, the concentration of the pesticide (e.g., methomyl) that was exposed to the fabric was proportional to the percent reduction of the pesticide. Without being bound by a particular theory, it is believed that the pesticide/halamine ratio is more critical to reduction than the actual contact time of the pesticide with the fabric. A pesticide to halamine ratio of about 10:1 to about 1:10 is suitable for the present methods, preferably, a ratio of about 5:1 to about 1:5 is used and, more preferably, a ratio of about 1:10 to about 1:1 is used. Table 1 sets forth various halogen ratios and percent reductions of various pesticides.

TABLE 1

| Pesticide | Pesticide/Chlorine Ratio | Pesticide Reduction (%) |
|---|---|---|
| Aldicarb | 1:5 | 99.54 |
| Methomyl | 1:4 | 79.52 |
| Carbofuran | 1:4 | 13.82 |
| Carbaryl | 1:4 | 8.02 |

In certain other aspects, the pesticide protective articles, such as pesticide protective clothing, possess regenerable and durable properties. For instance, after effective detoxification of a pesticide is obtained, the article can be rendered capable of possessing detoxification properties again. As illustrated in FIG. 2, the detoxification process on treated fabrics is completed after removal of the degraded pesticides on the surface of fabrics by laundering. In order to verify the mechanism as set forth in FIG. 2, re-bleached fabrics that were previously exposed to pesticides, demonstrated the ability to detoxify pesticides again. The previously exposed fabrics exhibited pesticide detoxification potential after laundering and re-bleaching, and therefore, it is concluded that the functional finishing is regenerable. As such, using the processes of the present invention, detoxifying properties are imparted onto articles, such as textiles, and these properties are regenerable.

Furthermore, the detoxifying properties imparted onto articles are durable. The durability of the process and its potential to continually detoxify pesticides was demonstrated through the percent reduction of pesticides of the article (e.g. finished fabrics) after laundering. A high percent reduction of pesticides (e.g. aldicarb) by fabrics that were laundered fifty times indicated that the detoxifying properties that were imparted were durable. Thus, the functional finishing on the cotton/polyester fabric is durable, surviving fifty equivalent regular machine washes without compromising its detoxification potential. This finished fabric can therefore provide optimum protection as well as comfort to the wearers.

EXAMPLES

The following examples are offered to illustrate, but not to limit the claimed invention.

MATERIALS

The selected textile materials were 65%/35% polyester/cotton (see, Table 2) blended fabrics, #7436 Dacron/cotton (available from Testfabrics Inc. Midlesex, N.J.). The compound used in fabric finishing was 1,3-dimethylol 5,5-dimethyl hydantoin (DMDMH) (Lonza Inc., Fairlawn, N.J.) (see, FIG. 3A). Sodium hypochlorite solution, was used in the halogenation (chlorination) of the: finished fabrics. The targeted pesticides were carbamates: methomyl (see, FIG. 3B) [S-methyl N-(methyl carbamoyloxy) thioacetimidatel] or Lannate®, (E.I. du Pont Nemours & Co. Inc., Wilmington Del.); aldicarb (see, FIG. 3C) [2-mesyl-2-methylpropionaldehydeO-methylcarbamoyloxime] (Riedel-de Haën). AATCC detergent 124 was used for all laundering. All other chemical reagents were purchased from Fisher Scientific.

TABLE 2

FABRIC CHARACTERIZATION

| Fiber Content | Fabric Number Weft | (yarns/cm) Warp | Fabric Weight ($g/m^2$) | Fabric Construction |
|---|---|---|---|---|
| 65%/35% Polyester/Cotton | 43 | 20 | 164 | plain weave |

TABLE 3

PHYSIOCHEMICAL AND BIOLOGICAL CHARACTERISTICS OF TARGETED CARBAMATES

| Pesticide | Molecular Formula | Molecular Weight (g/m) | Vapor Pressure mm Hg (25–30° C.) | Toxicity, mg/kg ($LD_{50}$, male rats) |
|---|---|---|---|---|
| Methomyl | $C_5H_{10}N_2O_2S$ | 162.2 | $5 \times 10^{-5}$ | 21 |
| Aldicarb | $C_7H_{14}N_2O_2S$ | 190.3 | $1 \times 10^{-4}$ | 1 |

METHODS

Polyester/cotton fabrics were washed in a domestic washing machine at 50° C. prior to the actual treatment of the functional compounds. The halamine functional compounds on the fabrics were achieved in two major steps: grafting a hydantoin ring onto the fabrics as the backbone for the functional compounds, followed by halogenation (e.g., chlorination) of the fabrics with hypochlorite bleach (e.g., CLOROX®).

The grafting of hydantoin ring onto the cotton/polyester fabrics was carried out using a wet finishing process. The weighed fabrics were submerged into an aqueous 6% (w/w) DMDMH solution for 5 min. and then wringed through a padder to secure a wet pickup of 70–100% through a 2 dip-2 nip cycle. These wet fabrics were then oven-dried at 85° C. for 5 min. and cured at 150° C. for 5 min. Following this, the fabrics were washed in water at 50° C. for 30 min. to remove any excess chemicals on the surface of the fabrics.

After the wet finishing process, the treated fabrics were bleached with solutions containing 0.01% and 0.1% (w/v) active chlorine content. The treated fabrics were submerged into aqueous bleach solution at one of the specified concentrations at 25° C. for 15 min. Then, the fabrics were air dried and stored at standard condition (25° C., 65% relative humidity). The chemically finished fabrics were then cut into 3×3 inches square swatches for exposure to pesticides in the subsequent testing.

Methomyl and aldicarb were dissolved in methanol at three different concentrations: 250, 500 and 1000 ppm. One mL of one of these pesticide solutions was directly loaded onto a fabric swatch. A contact time of 5 min. was allowed before the exposed fabric was extracted in organic solvent for detoxification assessment and degradation analysis. Fabrics that were not treated with DMDMH and bleach were also used as control samples.

The extraction of the exposed swatches was done by soaking a swatch into an initial volume of 50 mL ethyl acetate for 15 min. with vigorous agitation. The extraction was repeated with another 50 mL of ethyl acetate; the combined 100 mL of the extracted solvent was reduced to 2 mL in volume by rotor-evaporation under partial vacuum at 40° C. To this 2-mL sample, 1 $\mu$L of 2-ethyl-5-methyl pyridine was added as an internal standard for quantitation during the chromatographic analysis. After which, 1 $\mu$L of the extracted sample was injected into a gas chromatograph.

Gas chromatography was performed on a Hewlett Packard 5890 series II GC, equipped with a nitrogen-phosphorus detector (NPD), using a 15 m×0.25 mm I.D. DB-1 column, 0.25 $\mu$m film (J&W Co.). The temperature program was initially set at 100° C. for 3 min., raised at a rate of 7° C./min. to 250° C. and held for 5 min. The injector and detector were set at 250° C. and 280° C. respectively. Helium was used as the carrier gas at a flow rate of 0.84 mL/min; hydrogen flow rate was 2.98 mL/min; nitrogen flow rate was 29.16 mL/min. A split injection was used at a split ratio of 25:1. The responses of the resulting peak areas and relative peak areas were integrated and recorded using a HP 3396 II integrator. For each sample, at least three or more repetitions at each condition were carried out.

The laundering tests were carried out using the Launder-O-Meter from Atlas Electric Devices Co., following AATCC #61-1994 (*American Association of Textile Chemists and Colorists*, Technical Manual, AATCC, Research Triangle Park, N.C., 1996, pp 92–95). Each sample (that was exposed to 1000 ppm aldicarb solution) was laundered at 25° C. for 45 min. using 0.225 g AATCC detergent 124 and 150 mL distilled water. Then, the sample was rinsed with distilled water and air dried before re-bleaching. Re-bleaching of a sample was done by using a bleach solution containing 0.01% active chlorine content prior to exposure to 1000 ppm aldicarb solution in the subsequent testing. After which, these samples were laundered four more times using the same method and identical conditions, air dried and re-bleached using the same bleach solution before exposing them to 1000 ppm aldicarb again. Finally, these samples were laundered five more times, air dried and re-bleached using the same bleach solution prior to the last exposure to 1000 ppm aldicarb solution. The total number of washes done on each sample equated to ten. The amounts of aldicarb reduction at each laundering interval were used to show the durability of the functional finishing on the fabrics.

Example 1

This Example illustrates the detoxification of three different concentrations of methomyl by halamine structures on fabrics.

Using the materials and methods sets forth above, three different concentrations of methomyl were detoxified by halamine structures on the fabrics. The results are summarized in FIG. 4. Relative peak area response factors (peak area response of pesticide divided by peak area response of internal standard) of the control fabrics were used to determine the original amount of pesticide on the fabrics at 0% reduction. The subsequent relative response factors at the various pesticide concentrations and active bleach contents were subtracted from this original vahle to calculate the amount of pesticide being decomposed by halamine compounds on the fabrics. After this difference was divided by the original amount, it was expressed as the percentage reduction of pesticide at those various concentrations.

Figure 4:
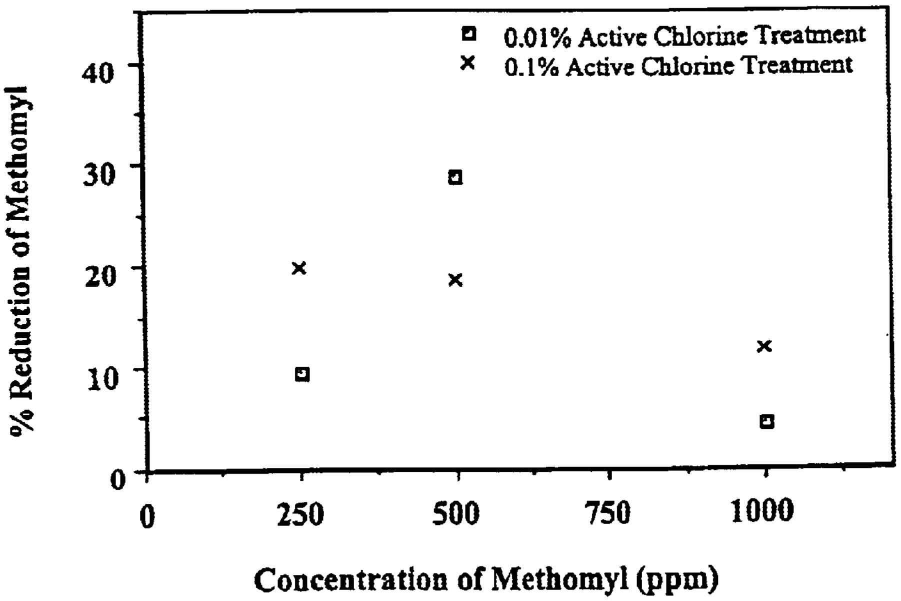
FIG. 4 illustrates the detoxification of methomyl by cotton/polyester fabrics treated with DMDMH.

As shown in FIG. 4, the concentration of active chlorine treatment affected the reduction of methomyl in two of the three concentration levels of 250 and 1000 ppm levels respectively. Higher concentration of active chlorine treatment led to increased reduction of methomyl on the fabrics. At the 250 ppm level, the percentage reduction of methomyl with the 0.01% active chlorine treatment (9.35%) was almost half ofthat at the 0.1% active chlorine treatment (19.90%). Similarly, the percentage reduction at 1000 ppm with 0.1% active chlorine treatment (11.63%) was almost three times as much as that of 0.01% (4.43%). This could be explained by the fact of a high concentration of chlorine i.e., more amine (nitrogen-hydrogen) groups on the hydantoin can be converted to active nitrogen-chlorine. Thus, more chlorine would be available on the fabric, increasing the amount of active moieties, which detoxify the methomyl on contact. Methomyl was found to disappear rapidly in aqueous solution at a chlorine/methomyl ratio of 10 to 1(see, Miles, C. J. and Oshiro, W. C., *Journal of Environmental Toxicology and Chemistry*, Vol. 9, 1990, p 535–540).

The effect of methomyl concentration could also be seen in the results. The reduction of methomyl and methomyl concentration were found to be inversely related. With the exception of the 500 ppm level, there was a decrease in the reduction of methomyl from the 250 to 1000 ppm levels in both of the 0.01% and 0.1% active chlorine treatments. With the chlorine content being held constant at both levels while the concentration of methomyl was increased from 250 to 1000 ppm, the ratio of chlorine to methomyl was actually decreased, leading to slower degradation of methomyl. This is reflected in the decrease in reduction of methomyl. The percentage reduction of methomyl at 250 ppm, 0.01% active chlorine treatment (9.4%) was more than double the reduction at 1000 ppm (4.4%). Similarly, at 0.1% active chlorine treatment, the percentage reduction of methomyl at 250 ppm (19.9%) was the highest, followed by that of 500 ppm (18.6%) and 1000 ppm (11.6%) showed lowest reduction. Since the chlorine/methomyl ratio was gradually decreased with increasing methomyl concentrations, the active chlorine moieties were also decreased, thus, retarding the degradation process (see, Miles, C. J. and Oshiro, W. C., *Journal of Environmental Toxicology and Chemistry*, Vol. 9, 1990, p535–540). With the gradual increase in methomyl concentration from 250 to 1000 ppm, the percent reduction at the 0.1% active chlorine treatment level slightly decreased.

Example 2

This Example illustrates chemical detoxification of aldicarb using methods of the present invention.

Figure 5:
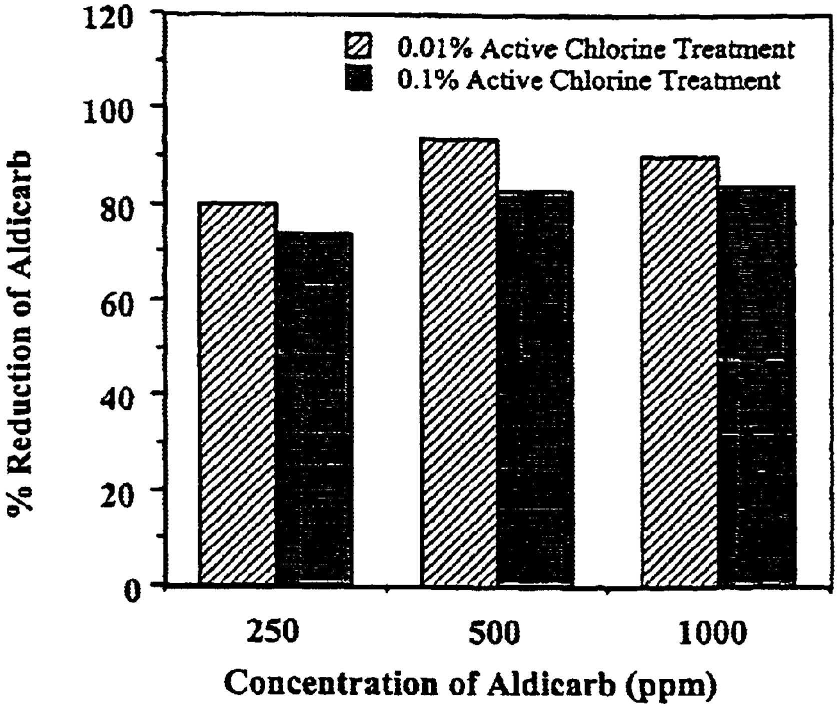
FIG. 5 illustrates the detoxification of aldicarb by cotton/polyester fabrics treated with DMDMH.

The results of a percent reduction of aldicarb by halamine structures on the fabrics are summarized in FIG. 5. The results from the detoxification of aldicarb showed a slight increase in the percentage reduction as the concentration was increased from 250 to 500 ppm for both active chlorine treatment. At the 250 ppm level, the percentage reduction of aldicarb for the 0.01% and 0.1% active chlorine treatment were close: 79.6% and 74.0%. In fact, effective detoxification and degradation of aldicarb could be achieved at 0.01% active chlorine content. Although higher levels of active chlorine treatment is also effective, from an economical point of view, the lowest possible concentration that yields comparatively effective results is most desirable.

Figure 6:
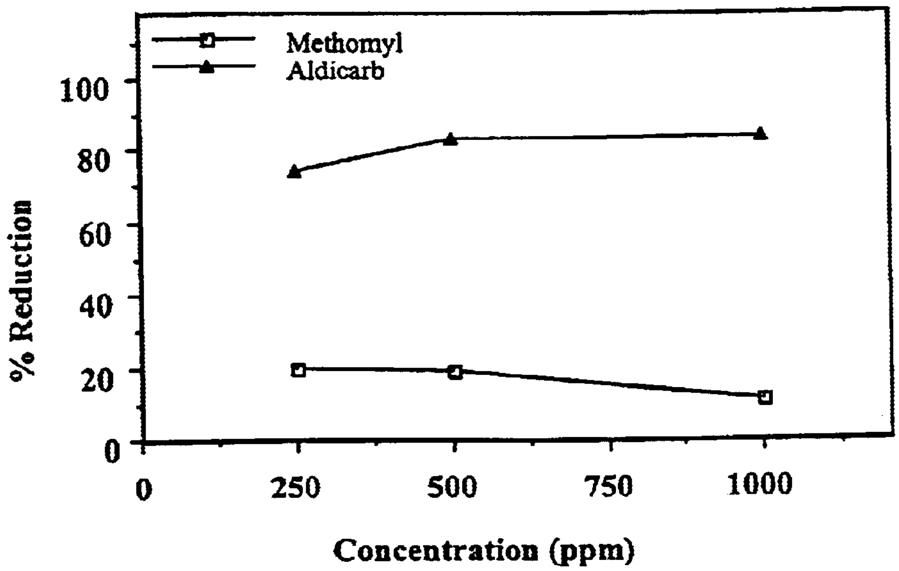
FIG. 6 illustrates reduction of methomyl and aldicarb at 0.1% active chlorine content.

In comparison, the percent reduction of aldicarb at all three concentrations was found to be much higher than that of methomyl. This difference in percent reduction became more apparent in FIG. 6, as the percentage reduction of the two pesticides was compared. The degradation of aldicarb by the halamine compound has proven to be more efficient than that of methomyl. The degradation of both aldicarb and methomyl begins when the molecules are broken down into smaller fragments. One such possibility is through oxidation.

The chemical structures of aldicarb and methomyl (see, FIG. 3 B and C), apart from the presence of an additional methyl group on aldicarb, the major difference between the two structures is the location and environment of the sulfur atoms. Without being bound by any particular theory, it is believed that being separated by two single bonds, both sulfur and carbon-nitrogen double bonds may become more vulnerable to chlorine oxidation. In the case of methomyl, delocalized lone pairs may be less attractive to chlorine on the halamine. However, in the case of aldicarb, the chlorine could possibly be drawn by both lone pairs on the sulfur as well as the nitrogen atoms, leading to the simultaneous break-down of aldicarb. Hence, the oxidation of this stabilized sulfur atom on methomyl would be slower than that on aldicarb, leading to slower degradation and lower reduction of methomyl.

Compared to the detoxification of methomyl, the reduction of aldicarb at all concentration levels (250, 500, 1000 ppm) was more effective and efficient. Over 70% reduction of aldicarb was attained at all pesticide concentrations for both levels of active chlorine treatment. Even at the lower level of 0.01% active chlorine content, almost 80% reduction was achieved at all pesticide concentrations. Due to the higher aldicarb reduction at this lower active chlorine treatment than the higher one, it can therefore be concluded that the concentration of active chlorine treatment is not as critical in the detoxification of aldicarb as in methomyl. Moreover, from an economical perspective, it could be suggested that an active chlorine treatment of 0.01% would be adequate for effective detoxification of the 1 mL aldicarb inoculation on cotton/polyester treated in 6% DMDMH solution.

Durability of the Functional Finishing

Figure 7:
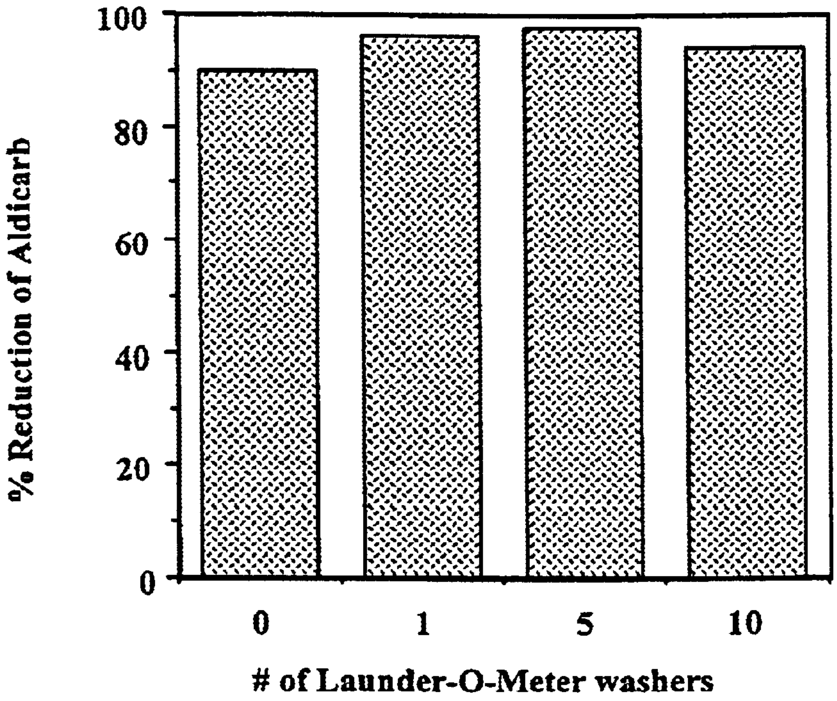
FIG. 7 illustrates detoxification of aldicarb on laundered fabrics that were treated with 6% DMDMH and 0.01% active chlorine content.

Results of the percentage reduction of aldicarb on laundered fabric samples are set forth in FIG. 7. The percentage reduction of aldicarb on all laundered fabric samples still remained well over 90%. This indicates that the relatively high reduction attained in the previous testing could be maintained even after laundering. According to the AATCC technical manual, one Launder-O-Meter wash is equivalent to five regular machine washes (see, American Association of Textile Chemists and Colorists, *Technical Manual*, AATCC, Research Triangle Park, N.C., 1996, pp 92–95). Also, a functional finishing that is considered durable on fabric is one that lasts for at least fifty regular machine washes. Hence, the treated fabrics showed excellent durability as well as outstanding pesticide detoxification potential even after fifty equivalent regular machine washes. This confirms that the fabric could indeed be considered as a regenerable, detoxifying pesticide protective clothing material, proving the initial hypothesis in the previously presented FIG. 2 to be valid.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A process for making a pesticide protective article, said process comprising:

(a) immersing said article in an aqueous treating solution which comprises a catalyst, a wetting agent and a non-aromatic heterocyclic amine selected from the group consisting of monomethylol-5,5-dimethylhydantoin (MDMH), 1,3-dimethylol-5,5-dimethylhydantoin (DMDMH); monoalkylolated and dialkylolated derivatives of 2,2,5,5-tetramethyl-1,3-imidazolidin-4-one, 6,6-dimethyl-1 ,3,5-triazine-2,4-dione, 4,4,5,5-tetramethyl-1,3-imidazolidin-2-one, cyanuric acid and 5,5-dimethylhydantoin; and monoalkyoxylated and dialkoxylated derivatives of monoalkylolated and dialkylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid, 5,5-dimethylhydantoin; and (b) treating said article with a halogenated aqueous solution, thereby making said pesticide protective article.

2. The process of claim 1, further comprising removing excess aqueous treating solution from said article before treating said article with a halogenated aqueous solution.

3. The process of claim 2, further comprising drying said article after removing excess aqueous treating solution to produce a dried article.

4. The process of claim 3, further comprising curing said dried article to produce a cured article.

5. The process of claim 4, further comprising washing said cured article to remove excess reagents.

6. The process of claim 5, further comprising drying said washed article to remove water.

7. The process of claim 1, wherein said article is a textile.

8. The process of claim 7, wherein said textile is a member selected from the group consisting of cellulosic fabric, cellulosic yarn, and cellulosic fiber.

9. The process of claim 7, wherein said textile is cotton fabric.

10. The process of claim 7, wherein said textile is cotton/polyester blend.

11. The process of claim 1, wherein said article is a polymer.

12. The process of claim 11, wherein said polymer is a member selected from the group consisting of cellulose and a synthetic polymer.

13. The process of claim 1, wherein said heterocyclic amine is 5,5-dimethylhydantoin.

14. The process of claim 1, wherein said pesticide is a member selected from the group consisting of herbicide, fungicide, rodenticide, insecticide and mixtures thereof.

15. The process of claim 1, wherein said pesticide is a member selected from the group consisting of methomyl, aldicarb, carbofuran, and carbaryl.

16. The process of claim 1, wherein said article is a wood product.

17. The process of claim 1, wherein said halogenated aqueous solution comprises sodium hypochlorite.

18. The process of claim 1, wherein said detoxification mechanism occurs through oxidation of said pesticide.

19. The process of claim 1, wherein said process is regenerable.

20. The process of claim 1, wherein said process is durable.

21. The process of claim 1, wherein said catalyst is a member selected from the group consisting of $MgCl_2$, $Mg(NO_3)_2$, $Zn(NO_3)_2$ and $NH_4NO_3$.

22. A process for detoxifying a pesticide, said process comprising: contacting said pesticide with an article having an N-halamine attached thereto, wherein said N-halamine is a non-aromatic heterocyclic amine selected from the group consisting of monomethylol-5,5-dimethylhydantoin (MDMH), 1,3-dimethylol-5,5-dimethylhydantoin (DMDMH); monoalkylolated and dialkylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid and 5,5-dimethylhydantoin; and monoalkyoxylated and dialkoxylated derivatives of monoalkylolated and dialkylolated derivatives of 2,2,5,5-tetramethyl-1,3-imidazolidin-4-one, 6,6-dimethyl-1,3,5-triazine-2,4-dione, 4,4,5,5-tetramethyl-1,3-imidazolidin-2-one, cyanuric acid, 5,5-dimethylhydantoin thereby detoxifying said pesticide.

23. The process of claim 22, wherein said article is a textile.

24. The process of claim 23, wherein said textile is a member selected from the group consisting of cellulosic fabric, cellulosic yarn, and cellulosic fiber.

25. The process of claim 23, wherein said textile is cotton fabric.

26. The process of claim 23, wherein said textile is cotton/polyester blend.

27. The process of claim 22, wherein said article is a polymer.

28. The process of claim 27, wherein said polymer is a member selected from the group consisting of cellulose and a synthetic polymer.

* * * * *